United States Patent
Ha et al.

(10) Patent No.: US 11,673,121 B2
(45) Date of Patent: Jun. 13, 2023

(54) CATALYST FOR OXIDATIVE COUPLING REACTION OF METHANE, METHOD FOR PREPARING THE SAME, AND METHOD FOR OXIDATIVE COUPLING REACTION OF METHANE USING THE SAME

(71) Applicant: KOREA INSTITUTE OF SCIENCE AND TECHNOLOGY, Seoul (KR)

(72) Inventors: Jeong-Myeong Ha, Seoul (KR); Lien Thi Do, Seoul (KR); Jae Wook Choi, Seoul (KR); Dong Jin Suh, Seoul (KR); Young Hyun Yoon, Seoul (KR); Gi Seok Yang, Seoul (KR); Hyun Joo Lee, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 17/553,795

(22) Filed: Dec. 17, 2021

(65) Prior Publication Data
US 2022/0203334 A1 Jun. 30, 2022

(30) Foreign Application Priority Data
Dec. 28, 2020 (KR) ........................ 10-2020-0184771

(51) Int. Cl.
*B01J 23/30* (2006.01)
*B01J 23/34* (2006.01)
(Continued)

(52) U.S. Cl.
CPC ............. *B01J 23/30* (2013.01); *B01J 21/063* (2013.01); *B01J 23/002* (2013.01); *B01J 23/34* (2013.01);
(Continued)

(58) Field of Classification Search
CPC . B01J 23/002; B01J 23/02; B01J 23/30; B01J 23/34; B01J 21/063; B01J 37/0009;
(Continued)

(56) References Cited

U.S. PATENT DOCUMENTS 9,718,054 B2 * 8/2017 Scher ................... B01J 37/0018
2014/0148610 A1 * 5/2014 Brazdil, Jr. .......... B01J 37/0045
558/324

FOREIGN PATENT DOCUMENTS

CN 105170138 A 12/2015
EP 3597290 1/2020
(Continued)

OTHER PUBLICATIONS

Yujin Sim et al., "Catalytic behavior of ABO3 perovskites in the oxidative coupling of methane," Molecular Catalysis, 2020, 11 pages, vol. 489, No. 110925.
(Continued)

*Primary Examiner* — In Suk C Bullock
*Assistant Examiner* — Jason Y Chong
(74) *Attorney, Agent, or Firm* — Cantor Colburn LLP

(57) ABSTRACT

Disclosed are a catalyst for oxidative coupling reaction of methane, a method for preparing the same, and a method for oxidative coupling reaction of methane using the same. The catalyst includes a mixed metal oxide, which is a mixed oxide of metals including sodium (Na), tungsten (W), manganese (Mn), barium (Ba) and titanium (Ti). It is possible to obtain paraffins, such as ethane and propane, and olefins, such as ethylene and propylene, with high efficiency through the method for oxidative coupling reaction of methane using the catalyst.

14 Claims, 1 Drawing Sheet

(51) Int. Cl.
- *B01J 21/06* (2006.01)
- *B01J 23/00* (2006.01)
- *B01J 37/04* (2006.01)
- *B01J 37/08* (2006.01)
- *B01J 37/00* (2006.01)
- *C07C 2/84* (2006.01)

(52) U.S. Cl.
CPC ............ *B01J 37/0036* (2013.01); *B01J 37/04* (2013.01); *B01J 37/08* (2013.01); *C07C 2/84* (2013.01); *C07C 2523/02* (2013.01); *C07C 2523/30* (2013.01); *C07C 2523/34* (2013.01)

(58) Field of Classification Search
CPC ........ B01J 37/0036; B01J 37/04; B01J 37/08; C07C 2523/02; C07C 2523/04; C07C 2523/30; C07C 2523/34; C07C 2521/06; C07C 9/06; C07C 11/04; Y02P 20/52
See application file for complete search history.

(56) References Cited

FOREIGN PATENT DOCUMENTS

| KR | 10-20190121391 A | 10/2019 |
| KR | 10-2020-0004678 A | 1/2020 |
| KR | 10-2020-0062459 A | 6/2020 |
| KR | 10-2021-0075374 A | 6/2021 |
| WO | 2011149996 A2 | 12/2011 |

OTHER PUBLICATIONS

English Translation of Notice of Allowance dated Dec. 19, 2002 in corresponding Korean patent application No. 10-2020-0184771, 2 pp.

Notice of Allowance dated Dec. 19, 2002 in corresponding Korean patent application No. 10-2020-0184771, 3 pp.

Seoyeon Lim et al., "Low-temperature oxidative coupling of methane using alkaline earth metaloxide-supported perovskites", Catalysis Today, 2020, vol. 352, pp. 127-133.

* cited by examiner

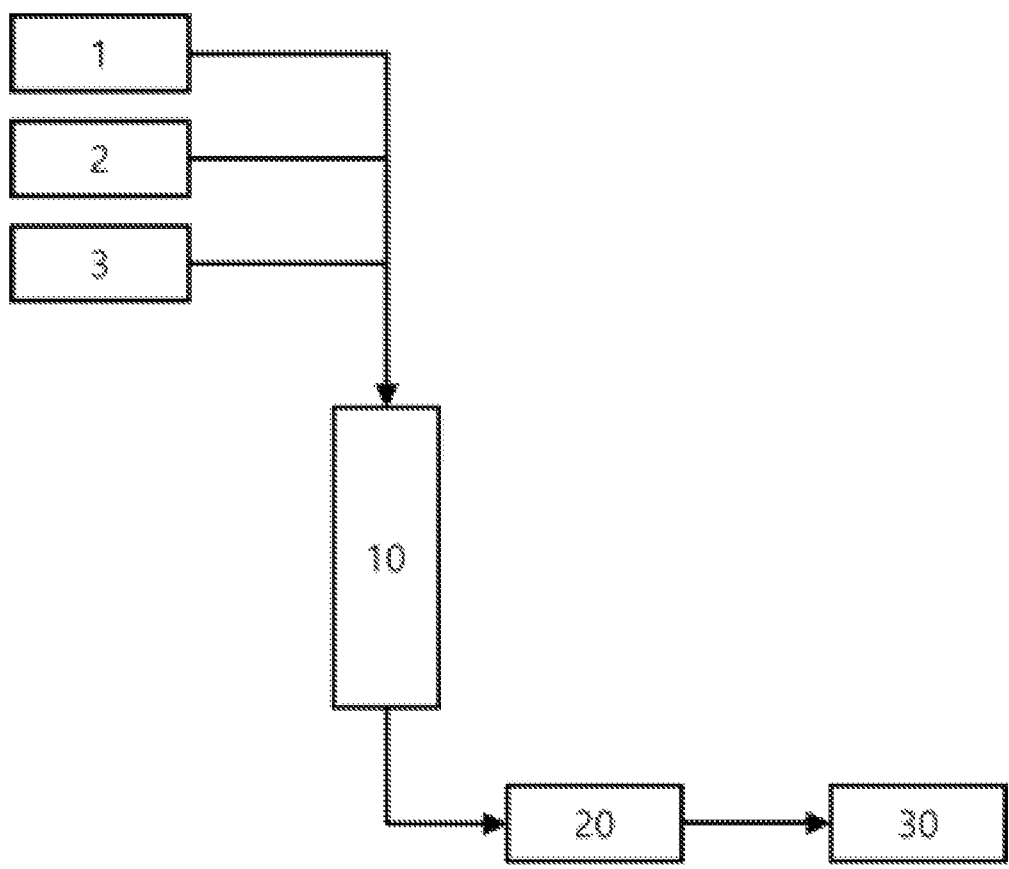

CATALYST FOR OXIDATIVE COUPLING REACTION OF METHANE, METHOD FOR PREPARING THE SAME, AND METHOD FOR OXIDATIVE COUPLING REACTION OF METHANE USING THE SAME

TECHNICAL FIELD

Cross-Reference to Related Applications

This application claims the priority of Korean Patent Application No. 10-2020-0184771, filed on Dec. 28, 2020 in the Republic of Korea, the contents of which in their entirety are herein incorporated by reference.

[Explanation on Nationally Supported Research and Development]

This research was conducted with the support of the Ministry of Science and ICT under the supervision of the Korea Institute of Science and Technology (specialized organization for research management: National Research Foundation of Korea, research business name: Research and Development (R&D) of Climate Change Response Technology, project title: Development of Technology of Catalyst for Producing Olefins through Oxidative Coupling of Methane, project number 1711104881).

The present disclosure relates to a catalyst for oxidative coupling reaction of methane, a method for preparing the same, and a method for oxidative coupling reaction of methane using the same.

BACKGROUND ART

Oxidative coupling reaction of methane is a reaction for producing paraffins, such as ethane and propane, and olefins, such as ethylene and propylene, through the reaction of methane, which is a main ingredient of natural gas, sale gas, bio-gas, or the like, under oxygen atmosphere. After converting methane into methyl radicals at a relatively high temperature, useful materials of fundamental chemistry can be produced through the coupling of methyl radicals and additional oxidation reaction.

In the oxidative coupling reaction of methane, a main reaction path for producing paraffins and olefins is as follows.

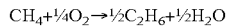

$CH_4 + \frac{1}{4}O_2 \rightarrow \frac{1}{2}C_2H_6 + \frac{1}{2}H_2O$

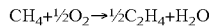

$CH_4 + \frac{1}{2}O_2 \rightarrow \frac{1}{2}C_2H_4 + H_2O$

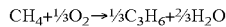

$CH_4 + \frac{1}{3}O_2 \rightarrow \frac{1}{3}C_3H_6 + \frac{2}{3}H_2O$

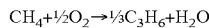

$CH_4 + \frac{1}{2}O_2 \rightarrow \frac{1}{3}C_3H_6 + H_2O$

A main reaction path for producing carbon dioxide ($CO_2$) and carbon monoxide (CO), which are byproducts, is as follows.

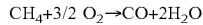

$CH_4 + 3/2\ O_2 \rightarrow CO + 2H_2O$

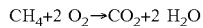

$CH_4 + 2\ O_2 \rightarrow CO_2 + 2\ H_2O$

Therefore, it is required to inhibit formation of carbon dioxide and carbon monoxide and to produce paraffins and olefins selectively in the oxidative coupling reaction of methane. For this purpose, there have been suggested various catalysts. However, since such catalysts cannot realize cost-efficiency sufficient for commercialization to date, there is a need for developing a catalyst capable of enhancing methane conversion in combination with selectivity to $C_{2+}$ compounds. There are many technical difficulties to enhance methane conversion and selectivity to $C_{2+}$ compounds even a little.

DISCLOSURE

Technical Problem

A technical problem to be solved by the present disclosure is to provide a catalyst for oxidative coupling reaction of methane.

Another technical problem to be solved by the present disclosure is to provide a method for preparing the catalyst for oxidative coupling reaction of methane.

Still another technical problem to be solved by the present disclosure is to provide a method for oxidative coupling reaction of methane by using the catalyst for oxidative coupling reaction of methane.

Technical Solution

In one general aspect, there is provided a catalyst for oxidative coupling reaction of methane, including a mixed metal oxide, which is a mixed oxide of metals including sodium (Na), tungsten (W), manganese (Mn), barium (Ba) and titanium (Ti).

According to an embodiment, the elemental ratio of W/Ti may be 0.04 to 1.39.

According to an embodiment, the elemental ratio of Mn/Ti may be 0.30 to 4.85.

According to an embodiment, the elemental ratio of Ba/Ti may be 0.8 to 1.5.

According to an embodiment, the elemental ratio of Mn/Na may be 0.5 or more.

In another general aspect, there is provided a method for preparing a catalyst for oxidative coupling reaction of methane, including the steps of: mixing and heating an aqueous precursor solution of sodium (Na), tungsten (W), manganese (Mn), barium (Ba) and titanium (Ti) metals with an organic acid to prepare a gel-like mixture; drying and pulverizing the gel-like mixture to obtain a pulverized product; and baking the pulverized product.

According to an embodiment, the organic acid may include citric acid.

According to an embodiment, the drying may be carried out at 50 to 150° C.

According to an embodiment, the baking may be carried out at 800 to 900° C.

In still another general aspect, there is provided a method for oxidative coupling reaction of methane, including adding the catalyst for oxidative coupling reaction of methane to methane to obtain hydrocarbon compounds containing two or more carbon atoms from methane.

According to an embodiment, the method for oxidative coupling reaction of methane may include the steps of: introducing a reaction mixture containing methane, oxygen and inert gas and the catalyst for oxidative coupling reaction of methane into a reactor, and carrying out oxidative coupling reaction of methane.

According to an embodiment, the oxidative coupling reaction of methane may be carried out at 600 to 850° C.

Advantageous Effects

According to the embodiments of the present disclosure, it is possible to provide a catalyst for oxidative coupling reaction of methane.

It is also possible to provide a method for preparing the catalyst for oxidative coupling reaction of methane.

In addition, it is possible to provide a method for oxidative coupling reaction of methane by using the catalyst for oxidative coupling reaction of methane.

BRIEF DESCRIPTION OF DRAWINGS

FIGURE is a schematic view illustrating the apparatus for oxidative coupling reaction of methane according to an embodiment of the present disclosure.

BEST MODE

Exemplary embodiments now will be described more fully hereinafter.

In one aspect of the present disclosure, there is provided a catalyst for oxidative coupling reaction of methane, including a mixed metal oxide, which is a mixed oxide of metals including sodium (Na), tungsten (W), manganese (Mn), barium (Ba) and titanium (Ti). The catalyst is for use in initiating oxidative coupling reaction of methane.

As used herein, the term '$C_{2+}$ compounds' refers to hydrocarbon compounds having two or more carbon atoms.

According to an embodiment, the elemental ratio of W/Ti may be 0.04 to 1.39. According to another embodiment, the elemental ratio of W/Ti may be 0.04 or more, 0.06 or more, 0.08 or more, 0.10 or more, 0.12 or more, 0.14 or more, 0.16 or more, 0.18 or more, or 0.20 or more, and 1.39 or less, 1.34 or less, 1.29 or less, 1.24 or less, 1.19 or less, 1.14 or less, 1.09 or less, 1.04 or less, 0.99 or less, 0.94 or less, 0.89 or less, 0.84 or less, 0.79 or less, 0.74 or less, 0.69 or less, 0.64 or less, 0.59 or less, 0.54 or less, 0.49 or less, 0.44 or less, 0.39 or less, 0.34 or less, 0.29 or less, 0.24 or less, 0.19 or less, or 0.14 or less. For example, the elemental ratio of W/Ti may be 0.06 to 0.18, 0.06 to 0.24, 0.12 to 0.18, 0.12 to 0.19, 0.12 to 0.20, 0.12 to 0.21, 0.12 to 0.22, 0.12 to 0.23, or 0.12 to 0.24, preferably.

According to an embodiment, the elemental ratio of Mn/Ti may be 0.30 to 4.85. According to another embodiment, the elemental ratio of Mn/Ti may be 0.30 or more, 0.32 or more, 0.42 or more, 0.52 or more, or 0.62 or more, and 4.85 or less, 3.85 or less, 2.85 or less, 1.85 or less, or 0.85 or less. For example, the elemental ratio of Mn/Ti may be 0.32 to 0.65, 0.32 to 0.81, 0.42 to 0.65, or 0.42 to 0.81, preferably.

According to an embodiment, the elemental ratio of Ba/Ti may be 0.8 to 1.5. According to another embodiment, the elemental ratio of Ba/Ti may be 0.8 or more, 0.9 or more, or 1.0 or more, and 1.5 or less, 1.4 or less, 1.3 or less, 1.2 or less, 1.1 or less, or 1.0 or less. For example, the elemental ratio of Ba/Ti may be 1.0 to 1.1 or 1.0 to 1.08, preferably.

According to an embodiment, the elemental ratio of Mn/Na may be 0.5 or more, particularly 0.5 to 5.0. According to another embodiment, the elemental ratio of Mn/Na may be 0.5 or more, 1.0 or more, 1.5 or more, 2.0 or more, 2.5 or more, 3.0 or more, 3.5 or more, 4.0 or more, or 4.5 or more, and 5.0 or less, 4.5 or less, 4.0 or less, 3.5 or less, 3.0 or less, 2.5 or less, 2.0 or less, 1.5 or less, or 1.0 or less. According to still another embodiment, the elemental ratio of Mn/Na may be 1.0 to 3.0 or 1.0 to 2.1.

The catalyst for oxidative coupling reaction of methane is effective for producing paraffin compounds, including ethane ($C_2H_6$) and propane ($C_3H_8$), and olefin compounds, including ethylene ($C_2H_4$) and propylene ($C_3H_6$), with high efficiency.

In another aspect of the present disclosure, three is provided a method for oxidative coupling reaction of methane, including the steps of: mixing and heating an aqueous precursor solution of sodium (Na), tungsten (W), manganese (Mn), barium (Ba) and titanium (Ti) metals with an organic acid to prepare a gel-like mixture; drying and pulverizing the gel-like mixture to obtain a pulverized product; and baking the pulverized product.

According to an embodiment, the precursor may be at least one selected from the group consisting of salt compounds, acetate compounds, halogen compounds, nitrate compounds, hydroxide compounds, carbonyl compounds, sulfate compounds and fatty acid salt compounds.

According to an embodiment, the aqueous precursor solution may include barium nitrate, sodium tungstate dihydrate, manganese nitrate hexahydrate and titanium isopropoxide.

According to an embodiment, the organic acid may include at least one of ascorbic acid, acetic acid and citric acid, particularly citric acid.

According to an embodiment, the organic acid may be citric acid preferably for preparing metal catalyst particles efficiently through the reduction of metal precursors.

According to an embodiment, the method may include mixing the aqueous precursor solution with the organic acid, and heating the resultant mixture at 80 to 100° C. to obtain a transparent gel-like mixture.

According to an embodiment, the drying may be carried out at 50 to 150° C.

According to an embodiment, the baking may be carried out at 800 to 900° C.

According to an embodiment, the baking may be carried out for 3 to 7 hours.

In still another aspect of the present disclosure, there is provided a method for oxidative coupling reaction of methane, including adding the catalyst for oxidative coupling reaction of methane to methane to obtain hydrocarbon compounds containing two or more carbon atoms from methane.

According to an embodiment, the hydrocarbon compounds containing two or more carbon atoms may be paraffins and/or olefins. Herein, the term 'paraffins' refers to alkane compounds having a molecular formula of $C_nH_{2n+2}$, and the term 'olefins' refers to alkene compounds having a molecular formula of $C_nH_{2n}$.

According to an embodiment, the method for oxidative coupling reaction of methane may include the steps of: introducing a reaction mixture containing methane, oxygen and inert gas and the catalyst for oxidative coupling reaction of methane into a reactor; and carrying out oxidative coupling reaction of methane.

According to an embodiment, methane and oxygen may be mixed at a volume ratio of 1:1 to 10:1.

According to an embodiment, the inert gas may be nitrogen.

According to an embodiment, the oxidative coupling reaction of methane may be carried out at 600 to 850° C. According to another embodiment, the oxidative coupling reaction of methane may be carried out at 600° C. or more, 625° C. or more, 650° C. or more, 675° C. or more, or 700° C. or more, and 850° C. or less, 825° C. or less, 800° C. or less, 775° C. or less, or 750° C. or less.

According to an embodiment, the oxidative coupling reaction of methane may be carried out at a gas hourly space velocity (GHSV) of 5,000 to 15,000 $h^{-1}$.

According to an embodiment, the oxidative coupling reaction of methane may be carried out in a continuous reactor (10) to which a heating device is linked.

The method for oxidative coupling reaction of methane is effective for producing paraffin compounds, including ethane ($C_2H_6$) and propane ($C_3H_8$), and olefin compounds, including ethylene ($C_2H_4$) and propylene ($C_3H_6$), with high efficiency.

Exemplary embodiments now will be described more fully hereinafter. The present disclosure may, however, be embodied in many different forms and should not be construed as limited to the exemplary embodiments set forth therein.

Example 1. Preparation of Catalyst

Mixed metal oxide catalysts for oxidative coupling reaction of methane were prepared in the manner as described hereinafter according to the compositions of ingredients as shown in the following Table 1. First, citric acid, barium nitrate and sodium tungstate dihydrate were mixed in 120 mL of ion exchange water, followed by agitation at room temperature for 10 minutes. Next, manganese nitrate hexahydrate and titanium isopropoxide were added thereto, and the resultant mixture was heated to 80° C. until a transparent gel was formed. The resultant mixture in the form of a gel was dried at 140° C. for 3 hours, pulverized into the form of powder, and calcined at 900° C. for 6 hours.

In addition, $Na_2WO_4/Mn/SiO_2$ catalyst known to provide high yield and selectivity was prepared as follows and compared with the mixed metal oxide catalysts as shown in Table 1. First, ethanol solution (100 mL) containing tetraethyl orthosilicate (TEOS) was agitated for 30 minutes to form a support. Aqueous nitric acid solution (5 to 10 mL, 66 wt %) was added to the support so as to accomplish pH 3, followed by agitation for 1 hour. Then, manganese nitrate hexahydrate was added dropwise thereto, and the resultant mixture was agitated for 30 minutes. In addition, sodium tungstate dihydrate was dissolved in 15 mL of ion exchange water, and the resultant solution was added dropwise to the mixture, followed by agitation at 65° C. for 48 hours. The resultant gel was dried under air at 105° C. for 16 hours, and then calcined under air at 800° C. for 5 hours to obtain the catalyst.

TABLE 1

| Catalysts | Sodium tungstate dihydrate (g) | Manganese nitrate hexahydrate (mL) | Barium nitrate (g) | Titanium isopropoxide (mL) | Citric acid (g) |
|---|---|---|---|---|---|
| $Ba_1Ti_1O_x$ | 0 | 0 | 6.34 | 7.33 | 18.54 |
| $Ba_{1.08}Ti_1O_x$ | 0 | 0 | 6.82 | 7.33 | 19.16 |
| $Mn_{0.8}Ba_1Ti_1O_x$ | 0 | 1.38 | 4.53 | 5.23 | 18.54 |
| $Na_{1.6}W_{0.8}Ba_1Ti_1O_x$ | 4.6 | 0 | 4.53 | 5.23 | 18.54 |
| $Na_{0.36}W_{0.18}Mn_{0.62}Ba_1Ti_1O_x$ | 1.0 | 1.07 | 4.53 | 5.23 | 18.54 |
| $Na_2W_1Mn_{3.5}O_x$ | 3.7 | 3.87 | 0 | 0 | 19.16 |
| $Na_{1.12}W_{0.56}Mn_{0.06}Ba_{1.08}Ti_1O_x$ | 3.4 | 0.11 | 5.28 | 5.62 | 19.16 |
| $Na_{0.42}W_{0.21}Mn_{0.42}Ba_{1.08}Ti_1O_x$ | 1.3 | 0.75 | 5.28 | 5.62 | 19.16 |
| $Na_{0.32}W_{0.16}Mn_{0.47}Ba_{1.08}Ti_1O_x$ | 0.93 | 0.84 | 5.28 | 5.62 | 19.16 |
| $Na_{0.28}W_{0.14}Mn_{0.49}Ba_{1.08}Ti_1O_x$ | 0.83 | 0.87 | 5.28 | 5.62 | 19.16 |
| $Na_{0.24}W_{0.12}Mn_{0.50}Ba_{1.08}Ti_1O_x$ | 0.75 | 0.90 | 5.28 | 5.62 | 19.16 |
| $Na_{0.20}W_{0.10}Mn_{0.52}Ba_{1.08}Ti_1O_x$ | 0.62 | 0.94 | 5.28 | 5.62 | 19.16 |
| $Na_{0.18}M_{0.09}Mn_{0.53}Ba_{1.08}Ti_1O_x$ | 0.53 | 0.96 | 5.28 | 5.62 | 19.16 |
| $Na_{0.12}W_{0.06}Mn_{0.56}Ba_{1.08}Ti_1O_x$ | 0.37 | 1.01 | 5.28 | 5.62 | 19.16 |
| $Na_{0.10}W_{0.05}Mn_{0.16}Ba_{1.08}Ti_1O_x$ | 0.33 | 0.35 | 6.20 | 6.59 | 19.16 |
| $Na_{0.18}W_{0.09}Mn_{0.32}Ba_{1.08}Ti_1O_x$ | 0.61 | 0.65 | 5.68 | 6.05 | 19.16 |
| $Na_{0.36}W_{0.18}Mn_{0.65}Ba_{1.08}Ti_1O_x$ | 1.05 | 1.11 | 4.87 | 5.18 | 19.16 |
| $Na_{0.46}W_{0.23}Mn_{0.81}Ba_{1.08}Ti_1O_x$ | 1.22 | 1.29 | 4.55 | 4.84 | 19.16 |
| $Na_{0.56}W_{0.28}Mn_{0.97}Ba_{1.08}Ti_1O_x$ | 1.38 | 1.45 | 4.26 | 4.53 | 19.16 |
| $Na_{0.64}W_{0.32}Mn_{1.13}Ba_{1.08}Ti_1O_x$ | 1.51 | 1.59 | 4.01 | 4.27 | 19.16 |
| $Na_{0.62}W_{0.31}Mn_{0.31}Ba_{1.08}Ti_1O_x$ | 1.87 | 0.56 | 5.28 | 5.62 | 19.16 |
| $Na_{2.77}W_{1.39}Mn_{4.85}Ba_{1.08}Ti_1O_x$ | 2.75 | 2.90 | 1.70 | 1.81 | 19.16 |

Example 2. Oxidative Coupling Reaction of Methane

Oxidative coupling reaction of methane was carried out by using a continuous fixed reactor (see, FIGURE). First, 0.2 g of each catalyst prepared from Example 1 was introduced to the continuous reactor, and a reaction mixture was introduced. The reaction mixture included methane, oxygen and nitrogen at a volume ratio of 3:1;1, and was introduced at a total flow rate of 0.54 mL/sec. The reaction temperature was selected in a range of 700 to 900° C., and the reaction product was analyzed quantitatively through gas chromatography with a flame ionization detector (GC-FID).

After carrying out the reaction, methane conversion and selectivity and yield of each of paraffin and olefin products were calculated according to the following formulas. The results are shown in the following Table 2 to Table 5.

Methane conversion (%)=(Number of moles of methane before reaction−Number of moles of methane after reaction)/(Number of moles methane before reaction)×100

Selectivity (%) to products having carbon number of n=n×(Number of moles of products having carbon number of n)/(Number of moles of methane before reaction−Number of moles of methane after reaction)×100

Yield (%) of products having carbon number of n=n×(Number of moles of products having carbon number of n)/(Number of moles of methane before reaction)×100

TABLE 2

| Catalysts | Reaction temperature (° C.) | Methane conversion (%) | C2+ Selectivity (%) | C2+ Yield (%) | Olefin Selectivity (%) | Olefin Yield (%) |
|---|---|---|---|---|---|---|
| $Na_{1.12}W_{0.56}Mn_{0.06}Ba_{1.08}Ti_1O_x$ | 700 | 3.9 | 28.0 | 1.1 | 3.3 | 0.1 |
| | 725 | 8.5 | 32.2 | 2.7 | 7.4 | 0.6 |
| | 750 | 12.3 | 41.6 | 5.1 | 9.9 | 1.2 |
| | 775 | 14.5 | 47.1 | 6.8 | 17.0 | 2.5 |
| | 800 | 17.5 | 49.1 | 8.6 | 24.3 | 4.3 |
| | 825 | 21.2 | 48.2 | 10.2 | 29.4 | 6.3 |
| | 850 | 47.5 | 47.1 | 22.4 | 29.2 | 13.9 |
| | 875 | 27.3 | 43.0 | 11.7 | 33.5 | 9.3 |
| | 900 | 27.4 | 39.6 | 10.9 | 32.8 | 9.4 |
| $Na_{0.62}W_{0.31}Mn_{0.31}Ba_{1.08}Ti_1O_x$ | 700 | 5.7 | 57.8 | 3.3 | 12.3 | 0.7 |
| | 725 | 31.7 | 65.5 | 20.8 | 34.4 | 10.9 |
| | 750 | 37.3 | 61.3 | 22.9 | 34.3 | 12.8 |
| | 775 | 36.3 | 61.5 | 22.3 | 38.3 | 14.0 |
| | 800 | 35.2 | 57.3 | 20.2 | 36.1 | 12.7 |
| | 850 | 33.0 | 55.4 | 18.3 | 40.1 | 13.5 |
| | 900 | 34,5 | 49.5 | 17.1 | 40.9 | 14.9 |
| $Na_{0.42}W_{0.21}Mn_{0.42}Ba_{1.08}Ti_1O_x$ | 700 | 35.6 | 66.7 | 23.8 | 37.6 | 13.4 |
| | 725 | 37.7 | 66.1 | 24.9 | 39.4 | 14.9 |
| | 750 | 37.8 | 65.2 | 24.7 | 40.1 | 15.2 |
| | 775 | 36.9 | 63.9 | 23.6 | 40.8 | 15.1 |
| | 800 | 34.2 | 62.6 | 21.4 | 39.9 | 13.7 |
| | 850 | 32.1 | 57.3 | 18.4 | 42.1 | 13.8 |
| | 900 | 30.32 | 51.0 | 15.5 | 42.4 | 13.7 |
| $Na_{0.32}W_{0.16}Mn_{0.47}Ba_{1.08}Ti_1O_x$ | 700 | 11.2 | 64.4 | 7.2 | 15.1 | 1.7 |
| | 725 | 38.3 | 66.6 | 25.5 | 39.9 | 15.4 |
| | 750 | 38.1 | 65.7 | 25.1 | 41.0 | 15.7 |
| | 775 | 37.6 | 64.7 | 24.3 | 41.5 | 15.8 |
| | 800 | 35.7 | 63.9 | 22.8 | 41.6 | 14.9 |
| | 850 | 33.1 | 59.5 | 19.7 | 44.0 | 14.9 |
| $Na_{0.28}W_{0.14}Mn_{0.49}Ba_{1.08}Ti_1O_x$ | 700 | 38.5 | 66.5 | 25.6 | 39.6 | 15.3 |
| | 725 | 38.4 | 65.7 | 25.2 | 40.2 | 15.5 |
| | 750 | 35.5 | 64.8 | 23.0 | 40.6 | 14.4 |
| | 775 | 35.0 | 63.7 | 22.3 | 41.2 | 14.5 |
| | 800 | 36.0 | 62.4 | 22.5 | 42.1 | 15.3 |
| $Na_{0.24}W_{0.12}Mn_{0.50}Ba_{1.08}Ti_1O_x$ | 700 | 35.0 | 66.1 | 23.1 | 38.4 | 13.5 |
| | 725 | 35.3 | 65.1 | 23.0 | 39.3 | 13.9 |
| | 750 | 35.5 | 64.3 | 22.8 | 40.1 | 14.3 |
| | 775 | 36.0 | 63.3 | 22.8 | 41.2 | 14.9 |
| | 800 | 35.4 | 61.1 | 21.6 | 43.0 | 15.4 |
| $Na_{0.20}W_{0.10}Mn_{0.52}Ba_{1.08}Ti_1O_x$ | 700 | 34.2 | 61.2 | 20.9 | 32.5 | 11.1 |
| | 725 | 35.3 | 61.8 | 21.8 | 34.4 | 12.2 |
| | 750 | 36.2 | 62.9 | 22.8 | 36.9 | 13.4 |
| | 775 | 36.9 | 63.5 | 23.5 | 39.4 | 14.6 |
| | 800 | 38.2 | 63.0 | 24.1 | 41.2 | 15.8 |

TABLE 3

| Catalysts | Reaction temperature (° C.) | Methane conversion (%) | C2+ Selectivity (%) | C2+ Yield (%) | Olefin Selectivity (%) | Olefin Yield (%) |
|---|---|---|---|---|---|---|
| $Na_{0.18}W_{0.09}Mn_{0.53}Ba_{1.08}Ti_1O_x$ | 700 | 32.8 | 63.9 | 21.0 | 36.7 | 12.1 |
| | 725 | 33.8 | 64.1 | 21.6 | 38.1 | 12.9 |
| | 750 | 35.1 | 63.7 | 22.4 | 39.0 | 13.7 |
| | 775 | 35.0 | 63.2 | 22.1 | 40.3 | 14.2 |
| | 800 | 33.1 | 61.9 | 20.5 | 41.2 | 13.7 |
| $Na_{0.12}W_{0.06}Mn_{0.56}Ba_{1.08}Ti_1O_x$ | 700 | 31.6 | 57.9 | 18.3 | 30.9 | 9.8 |
| | 725 | 32.4 | 59.5 | 19.3 | 33.1 | 10.8 |
| | 750 | 33.1 | 60.9 | 20.2 | 35.5 | 11.8 |
| | 775 | 35.1 | 60.7 | 21.3 | 37.0 | 13.0 |
| | 800 | 34.8 | 59.1 | 20.6 | 38.2 | 13.4 |
| $Ba_{1.08}Ti_1O_x$ | 700 | 30.6 | 45.4 | 13.9 | 21.4 | 6.6 |
| | 725 | 34.4 | 47.5 | 16.3 | 23.7 | 8.2 |
| | 750 | 34.1 | 49.0 | 16.7 | 24.4 | 8.3 |
| | 775 | 33.7 | 49.3 | 16.6 | 25.9 | 8.7 |
| | 800 | 34.6 | 49.7 | 17.2 | 27.7 | 9.6 |
| $Na_{0.1}W_{0.05}Mn_{0.16}Ba_{1.08}Ti_1O_x$ | 700 | 25.1 | 36.0 | 9.0 | 13.5 | 3.4 |
| | 725 | 25.8 | 37.5 | 9.7 | 13.5 | 3.5 |
| | 750 | 25.2 | 38.3 | 9.6 | 14.8 | 3.7 |
| | 775 | 27.0 | 39.1 | 10.5 | 16.9 | 4.6 |
| | 800 | 27.1 | 40.0 | 10.9 | 19.8 | 5.4 |

TABLE 3-continued

| Catalysts | Reaction temperature (° C.) | Methane conversion (%) | C2+ Selectivity (%) | C2+ Yield (%) | Olefin Selectivity (%) | Olefin Yield (%) |
|---|---|---|---|---|---|---|
| $Na_{0.18}W_{0.09}Mn_{0.32}Ba_{1.08}Ti_1O_x$ | 700 | 26.9 | 64.3 | 17.3 | 32.4 | 8.7 |
| | 725 | 31.3 | 64.4 | 20.1 | 36.2 | 11.4 |
| | 750 | 33.1 | 63.3 | 21.0 | 37.4 | 12.4 |
| | 775 | 33.3 | 63.2 | 21.0 | 39.6 | 13.3 |
| | 800 | 33.0 | 62.1 | 20.5 | 41.2 | 13.7 |
| $Na_{0.36}W_{0.18}Mn_{0.85}Ba_{1.08}Ti_1O_x$ | 700 | 39.1 | 66.3 | 25.9 | 38.5 | 15.1 |
| | 725 | 38.9 | 65.5 | 25.5 | 39.6 | 15.4 |
| | 750 | 38.4 | 64.7 | 24.9 | 40.2 | 15.5 |
| | 775 | 37.7 | 63.4 | 23.9 | 40.8 | 15.5 |
| | 800 | 35.8 | 62.0 | 22.2 | 42.2 | 15.2 |
| | 825 | 35.8 | 60.4 | 21.6 | 42.2 | 15.3 |
| | 850 | 33.4 | 57.8 | 19.3 | 42.9 | 14.6 |
| | 875 | 32.6 | 54.7 | 17.9 | 43.3 | 14.6 |
| | 900 | 31.9 | 50.8 | 16.2 | 42.3 | 14.3 |

TABLE 4

| Catalysts | Reaction temperature (° C.) | Methane conversion (%) | C2+ Selectivity (%) | C2+ Yield (%) | Olefin Selectivity (%) | Olefin Yield (%) |
|---|---|---|---|---|---|---|
| $Na_{0.46}W_{0.23}Mn_{0.81}Ba_{1.08}Ti_1O_x$ | 700 | 7.8 | 67.4 | 5.2 | 15.8 | 1.2 |
| | 725 | 35.3 | 65.5 | 23.2 | 39.7 | 14.0 |
| | 750 | 34.5 | 64.5 | 22.3 | 40.5 | 14.0 |
| | 775 | 35.4 | 63.3 | 22.4 | 41.4 | 14.7 |
| | 800 | 35.4 | 61.1 | 21.6 | 43.2 | 15.4 |
| $Na_{0.56}W_{0.28}Mn_{0.97}Ba_{1.08}Ti_1O_x$ | 700 | 8.9 | 67.3 | 6.0 | 16.8 | 1.5 |
| | 725 | 34.3 | 65.9 | 22.6 | 39.5 | 13.6 |
| | 750 | 36.3 | 64.8 | 23.5 | 40.5 | 14.7 |
| | 775 | 35.2 | 63.3 | 22.3 | 41.1 | 14.5 |
| | 800 | 34.4 | 60.5 | 20.8 | 42.4 | 14.7 |
| $Na_{0.64}W_{0.32}Mn_{1.13}Ba_{1.08}Ti_1O_x$ | 700 | 3.4 | 64.8 | 2.2 | 13.5 | 0.5 |
| | 725 | 16.5 | 70.9 | 11.7 | 31.2 | 5.2 |
| | 750 | 34.4 | 64.7 | 22.2 | 40.5 | 13.9 |
| | 775 | 34.0 | 63.1 | 21.4 | 41.2 | 14.1 |
| | 800 | 32.7 | 60.2 | 19.7 | 42.5 | 14.0 |
| $Na_{2.77}W_{1.39}Mn_{4.85}Ba_{1.08}Ti_1O_x$ | 700 | 6.1 | 63.3 | 3.9 | 14.7 | 0.9 |
| | 725 | 31.5 | 67.2 | 21.2 | 36.8 | 11.6 |
| | 750 | 33.6 | 64.2 | 21.6 | 38.1 | 12.8 |
| | 775 | 32.4 | 61.1 | 19.8 | 38.0 | 12.3 |
| | 800 | 31.2 | 58.4 | 18.3 | 37.9 | 11.9 |
| $Na_2W_1Mn_{3.5}O_x$ | 700 | 2.0 | 27.5 | 0.5 | 0.0 | 0.0 |
| | 725 | 5.2 | 26.7 | 1.4 | 3.0 | 0.2 |
| | 750 | 8.1 | 34.7 | 2.8 | 6.6 | 0.5 |
| | 775 | 5.5 | 42.7 | 2.4 | 15.0 | 0.8 |
| | 800 | 8.6 | 50.7 | 4.3 | 19.6 | 1.7 |
| $Ba_1Ti_1O_x$ | 700 | 29.6 | 48.6 | 14.4 | 22.6 | 6.7 |
| | 725 | 30.5 | 49.6 | 15.1 | 23.2 | 7.1 |
| | 750 | 30.8 | 50.3 | 15.5 | 24.6 | 7.6 |
| | 775 | 31.2 | 50.9 | 15.9 | 26.2 | 8.2 |
| | 800 | 29.6 | 50.4 | 14.9 | 28.8 | 8.6 |

TABLE 5

| Catalysts | Reaction temperature (° C.) | Methane conversion (%) | C2+ Selectivity (%) | C2+ Yield (%) | Olefin Selectivity (%) | Olefin Yield (%) |
|---|---|---|---|---|---|---|
| $Mn_{0.8}Ba_1Ti_1Ox$ | 700 | 19.7 | 10.0 | 2.0 | 3.6 | 0.7 |
| | 725 | 20.3 | 10.2 | 2.1 | 3.8 | 0.8 |
| | 750 | 21.8 | 11.2 | 2.4 | 3.5 | 0.8 |
| | 775 | 21.0 | 13.8 | 2.9 | 5.3 | 1.1 |
| | 800 | 19.9 | 15.8 | 3.2 | 7.2 | 1.4 |

TABLE 5-continued

| Catalysts | Reaction temperature (° C.) | Methane conversion (%) | C2+ Selectivity (%) | C2+ Yield (%) | Olefin Selectivity (%) | Olefin Yield (%) |
|---|---|---|---|---|---|---|
| $Na_{1.8}W_{0.8}Ba_1Ti_1O_x$ | 700 | 1.3 | 18.9 | 0.2 | 0.0 | 0.0 |
|  | 725 | 1.7 | 18.1 | 0.3 | 1.8 | 0.0 |
|  | 750 | 3.0 | 20.8 | 0.6 | 3.4 | 0.1 |
|  | 775 | 4.3 | 25.6 | 1.1 | 6.1 | 0.3 |
|  | 800 | 5.5 | 32.0 | 1.8 | 9.8 | 0.5 |
| $Na_{0.36}W_{0.18}Mn_{0.62}Ba_1Ti_1O_x$ | 700 | 34.1 | 64.6 | 22.0 | 36.7 | 12.5 |
|  | 725 | 35.1 | 64.5 | 22.6 | 37.7 | 13.2 |
|  | 750 | 34.0 | 63.7 | 21.6 | 38.2 | 13.0 |
|  | 775 | 34.6 | 62.4 | 21.6 | 38.3 | 13.3 |
|  | 800 | 35.9 | 60.6 | 21.7 | 37.9 | 13.6 |
| $Na_2WO_4/Mn/SiO_2$ | 700 | 8.3 | 49.0 | 4.0 | 14.7 | 1.2 |
|  | 725 | 21.0 | 61.7 | 12.9 | 27.5 | 5.8 |
|  | 750 | 35.9 | 63.9 | 22.9 | 40.2 | 14.5 |
|  | 775 | 36.3 | 62.9 | 22.8 | 42.9 | 15.7 |
|  | 800 | 35.8 | 61.8 | 22.1 | 43.0 | 15.6 |

As a result, the catalysts, $Na_{0.62}W_{0.31}Mn_{0.31}Ba_{1.08}Ti_1O_x$, $Na_{0.42}W_{0.21}Mn_{0.42}Ba_{1.06}Ti_1O_x$, $Na_{0.32}W_{0.16}Mn_{0.47}Ba_{1.08}Ti_1O_x$, $Na_{0.28}W_{0.14}Mn_{0.49}Ba_{1.06}Ti_1O_x$, $Na_{0.24}W_{0.12}Mn_{0.50}Ba_{1.08}Ti_1O_x$, $Na_{0.20}W_{0.10}Mn_{0.52}Ba_{1.08}Ti_1O_x$, $Na_{0.18}W_{0.09}Mn_{0.53}Ba_{1.08}Ti_1O_x$, $Na_{0.12}W_{0.06}Mn_{0.56}Ba_{1.08}Ti_1O_x$, $Na_{0.18}W_{0.09}Mn_{0.32}Ba_{1.08}Ti_1O_x$, $Na_{0.36}W_{0.18}Mn_{0.65}Ba_{1.08}Ti_1O_x$, $Na_{0.46}W_{0.23}Mn_{0.81}Ba_{1.08}Ti_1O_x$, $Na_{0.56}W_{0.28}Mn_{0.97}Ba_{1.08}Ti_1O_x$, $Na_{0.64}W_{0.32}Mn_{1.13}Ba_{1.08}Ti_1O_x$, $Na_{2.77}W_{1.39}Mn_{4.85}Ba_{1.08}Ti_1O_x$ and $Na_{0.36}W_{0.18}Mn_{0.65}Ba_{1.07}Ti_1O_x$ showed a high $C_{2+}$ yield of 20% or more under the reaction condition of 700 to 800° C. Particularly, the catalyst, $Na_{0.36}W_{0.16}Mn_{0.65}Ba_{1.08}Ti_1O_x$ showed high activities of a methane conversion of 39.1%, $C_{2+}$ selectivity of 66.3%, $C_{2+}$ yield of 25.9%, olefin selectivity of 38.5%, and olefin yield of 15.1% at a low reaction temperature of 700° C., which are significantly higher activities as compared to the activities (methane conversion of 8.3%, $C_{2+}$ selectivity of 49.0%, $C_{2+}$ yield of 4.0%, olefin selectivity of 14.7%, and olefin yield of 1.2%) obtained by using a conventional catalyst for oxidative coupling reaction of methane, i.e. $Na_2WO_4/Mn/SiO_2$, at 700° C. As stated above, the mixed metal oxide catalyst according to the present disclosure provides a $C_{2+}$ yield of approximately 25% under a low reaction temperature condition. Therefore, it can be seen that the mixed metal oxide catalyst is effective for significantly enhancing the cost-efficiency and efficiency of oxidative coupling reaction of methane.

The present disclosure has been described in detail. It will be apparent to those skilled in the art that the description proposed herein is just a preferable example for the purpose of illustrations only, not intended to limit the scope of the disclosure, so it should be understood that other equivalents and modifications could be made thereto without departing from the scope of the disclosure.

DESCRIPTION OF DRAWING NUMERALS

1: Methane gas cylinder
2: Oxygen gas cylinder
3: Nitrogen gas cylinder
10: Reactor and electric furnace
20: Cooler
30: Gas chromatography system

The invention claimed is:

1. A catalyst for oxidative coupling reaction of methane, comprising a mixed metal oxide, which is a mixed oxide of metals comprising sodium (Na), tungsten (W), manganese (Mn), barium (Ba) and titanium (Ti); wherein the elemental ratio of Mn/Na is 1.0 or more.

2. The catalyst for oxidative coupling reaction of methane according to claim 1, wherein the elemental ratio of W/Ti is 0.04 to 0.44.

3. The catalyst for oxidative coupling reaction of methane according to claim 1, wherein the elemental ratio of Mn/Ti is 0.30 to 2.85.

4. The catalyst for oxidative coupling reaction of methane according to claim 1, wherein the elemental ratio of Ba/Ti is 0.8 to 1.5.

5. The catalyst for oxidative coupling reaction of methane according to claim 1, wherein the elemental ratio of Mn/Na is 1.5 or more.

6. A catalyst for oxidative coupling reaction of methane, comprising a mixed metal oxide, which is a mixed oxide of metals comprising sodium (Na), tungsten (W), manganese (Mn), barium (Ba) and titanium (Ti);
wherein the elemental ratio of Mn/Na is 1.0 or more;
wherein the elemental ratio of Mn/Ti is 0.32 to 0.65; and
wherein the elemental ratio of W/Ti is 0.1 to 0.49.

7. A method for preparing the catalyst for oxidative coupling reaction of methane according to claim 1, comprising the steps of:
mixing and heating an aqueous precursor solution of sodium (Na), tungsten (W), manganese (Mn), barium (Ba) and titanium (Ti) metals with an organic acid to prepare a gel;
drying and pulverizing the gel-like mixture to obtain a pulverized product; and
baking the pulverized product to obtain the catalyst.

8. The method for preparing the catalyst for oxidative coupling reaction of methane according to claim 7, wherein the organic acid comprises citric acid.

9. The method for preparing the catalyst for oxidative coupling reaction of methane according to claim 7, wherein the drying is carried out at 50-150° C.

10. The method for preparing the catalyst for oxidative coupling reaction of methane according to claim 7, wherein the baking is carried out at 800-900° C.

11. The method for preparing the catalyst for oxidative coupling reaction of methane according to claim 7, wherein the elemental ratio of Mn/Ti is 0.32 to 0.65, and the elemental ratio of W/Ti is 0.1 to 0.49.

12. A method for oxidative coupling reaction of methane, comprising contacting methane with the catalyst for oxidative coupling reaction of methane according to claim 1 to obtain hydrocarbon compounds containing two or more carbon atoms from methane.

13. The method for oxidative coupling reaction of methane according to claim 12, which comprises the steps of:
  introducing a reaction mixture comprising methane, oxygen and inert gas and the catalyst for oxidative coupling reaction of methane into a reactor; and
  carrying out oxidative coupling reaction of methane.

14. The method for oxidative coupling reaction of methane according to claim 13, wherein the oxidative coupling reaction of methane is carried out at 600 to 850° C.

* * * * *